United States Patent
Striggow et al.

(10) Patent No.: US 7,645,461 B2
(45) Date of Patent: Jan. 12, 2010

(54) METHOD OF TREATING CEREBRAL ISCHEMIA WITH HYDROGENATION PRODUCTS OF FRANKINCENSE EXTRACTS

(75) Inventors: Frank Striggow, Gerwisch (DE); Werner Schmidt, Magdeburg (DE); Till Mack, Magdeburg (DE)

(73) Assignee: Key Neurotek AG, Magdeburg (DE)

( * ) Notice: Subject to any disclaimer, the term of this patent is extended or adjusted under 35 U.S.C. 154(b) by 0 days.

(21) Appl. No.: 10/549,323

(22) PCT Filed: Mar. 18, 2004

(86) PCT No.: PCT/EP2004/002839

§ 371 (c)(1),
(2), (4) Date: Sep. 26, 2005

(87) PCT Pub. No.: WO2004/082699

PCT Pub. Date: Sep. 30, 2004

(65) Prior Publication Data

US 2006/0177467 A1  Aug. 10, 2006

(30) Foreign Application Priority Data

Mar. 18, 2003 (DE) ............................... 103 11 920
Mar. 18, 2003 (DE) ............................... 103 11 921
Jul. 14, 2003 (DE) ............................... 103 31 750

(51) Int. Cl.
*A61K 36/00* (2006.01)
*A61K 31/00* (2006.01)
*A01K 26/00* (2006.01)
*A01N 61/00* (2006.01)

(52) U.S. Cl. ........................................ 424/725; 514/1
(58) Field of Classification Search .................. None
See application file for complete search history.

(56) References Cited

U.S. PATENT DOCUMENTS 5,720,975 A * 2/1998 Etzel ........................... 424/464

6,280,751 B1  8/2001  Fletcher et al. ............. 424/401

OTHER PUBLICATIONS

Singer PA, Wasserman, RE and Hanna GR. 'Associated systemic factors in cerebrovascular ischemia', South Med J. vol. 69, No. 6 (Jun. 1976) pp. 709-714.*
Braune HJ, Munk MH and Huffmann G. 'Cerebral infarct in the circulatory area of the arterial cerebral media following chiropractic therapy of the cervical spine', Dtsch Med Wochenschr, vol. 116, No. 27 (Jul. 1991) pp. 1047-1050.*
Koudstaal PJ. 'Anticoagulant treatment in stroke prevention'. Rev Neurol (Paris). vol. 155, No. 9 (1999), pp. 694-696.*
Chen et al. "Combination therapy for ischemic stroke: potential of neuroprotectants plus thrombolytics". Am. J. Cardiovasc. Drugs, vol. 2, No. 5 (2002) 303-313, Abstract only.*
PCMR Research: Animal Experimentation Issues. Internet archive date: Feb. 27, 2003 [Retrieved from the internet: Jul. 29, 2008]. Retrieved from: http://web.archive.org/web/*/http://www.pcrm.org/resch/anexp/rats.html.*
Badria FA, Mikhaeil BR, Maatooq GT, Amer MM. Immunomodulatory triterpenoids from the oleogum resin of Boswellia carterii Birdwood. Z Naturforsch [Jul.-Aug. 2003] vol. 58, No. 7-8. pp. 505-516. PubMed Abstract only.*
International Search Report issued in PCT/EP04/02839.
Wang, W, WPI Database No. XP-002291633, Derwent Publications Ltd. (1995)—Abstract only.
International Preliminary Report on Patentability (Chapter I) issued in PCT/EP04/002839 (Oct. 6, 2005), abstract only.
English translation of the International Preliminary Report on Patentability (Chapter I) issued in PCT/EP04/002839 (Mar. 2, 2006).

* cited by examiner

*Primary Examiner*—Christopher R Tate
*Assistant Examiner*—Amy L Clark

(57) ABSTRACT

The invention relates to the use of the hydrogenation products of frankincense (olibanum), its hydrogenated ingredients as well as physiologically acceptable salts and derivatives thereof and hydrogenated frankincense extracts for the production of a medicament for the prophylactic and/or therapeutic treatment of cerebral ischemia, cranial/brain trauma and/or Alzheimer's disease. The use of frankincense, frankincense extract, substances contained in frankincense, their physiologically acceptable salts, their derivatives and the physiological salts thereof, pure boswellic acids, tirucallic acids or other triterpenes, their physiologically acceptable salts, derivatives of the salts thereof for the production of a medicament for the prophylactic and/or therapeutic treatment of cerebral ischemia and/or cranial/brain trauma is also provided according to the invention.

10 Claims, No Drawings

METHOD OF TREATING CEREBRAL ISCHEMIA WITH HYDROGENATION PRODUCTS OF FRANKINCENSE EXTRACTS

This application claims priority to German Patent Application Nos. 103 11 920.5 filed Mar. 18, 2003, 103 11 921.3 filed Mar. 18, 2003, and 103 31 750.3 filed Jul. 14, 2003, the contents of which are incorporated by reference herein in their entirety.

The invention relates to the use of frankincense or components thereof, which may be hydrogenated, where appropriate, for preventing and/or treating cerebral ischemia and/or cranial/brain trauma. It has also been found that the hydrogenation products of frankincense or the components thereof are particularly advantageous in preventing and/or treating Alzheimer's disease.

The invention thus relates in particular to the use of the hydrogenation products of frankincense (olibanum), its hydrogenated ingredients as well as physiologically acceptable salts and derivatives thereof for the production of a medicament for preventing and/or treating cerebral ischemia, cranial/brain trauma and/or Alzheimer's disease. The invention also relates to the use of frankincense or components of frankincense for the production of a medicament for preventing and/or treating cerebral ischemia and/or cranial/brain trauma (traumatic brain injury, TBI).

Ischemia is the interrupted supply of blood to cells, tissues or organs. This situation is critical in particular if a continuous supply with oxygen and/or nutrients (e.g. glucose) is necessary. This applies in particular to the central nervous system (CNS), since the very nerve cells extremely respond to an interruption of oxygen and glucose supplies. Short-term ischemia, e.g. as a result of an apoplexy or a cardiac infarction, already results in neuronal cell death in the affected brain centers.

The cellular mechanisms of ischemia-induced lesion processes are complex and have been comprehended insufficiently in their complexity to date. Thus, effective preventive measures and therapies are problematic.

A cranial/brain trauma is understood to mean a combined injury of scalp, cranium and brain, the outer cover possibly remaining intact. A distinction is generally made between an open cranial/brain trauma and a closed cranial/brain trauma, the dura being destroyed in an open cranial/brain trauma with fluid and/or brain substance escaping. The blunt or closed brain trauma differs therefrom in so far as the dura is not destroyed.

The skull and/or brain injuries accompanying a cranial/brain trauma increase the intracranial pressure thus damaging various brain centers. Neuronal lesion processes indicated in such a way can influence cognitive, patient's physical and psychic properties, the cellular mechanisms of traumatic lesion processes being complex and only comprehend insufficiently in their complexity to date.

Although various therapeutic methods are known for cerebral ischemia or cranial/brain trauma, there is a considerable need for a therapeutic method preventing in particular nerve cells from dieing off and, in the case of a cranial/brain trauma, in particular also the occurrence of trauma-induced lesions.

Alzheimer's disease is a degenerative disease causing morphological and biochemical changes of brain centers. It is a progressive atrophy of the cerebral cortex with senile plaques, degeneration of neurofibrils and congophilic angiopathy. The symptoms of Alzheimer's disease are inter alia disorientation accompanied by disturbances of cognitive ability, memory decay, total regression up to dementia. A disturbance of the cortical cholinergic system accompanied by a reduction of choline acetylase (reduced acetylcholine synthesis) is inter alia detectable biochemically.

The causes of the development of Alzheimer's disease are unclear, with genetic, metabolic or even slow virus infections being predominantly discussed. Therapeutic agents having specific actions are not yet available. The therapeutic possibilities extend above all to the alleviation of symptoms caused by the diseases. In order to treat Alzheimer's disease, e.g. the choline esterase inhibitor tacrin is used, which shall improve cognitive performance. However, a therapy using this active substance is unsatisfactory because of its small response rate and its strong side-effects. Therefore, there is a strong demand for a therapeutic method which at least delays the brain atrophy progression in Alzheimer's patients. There is also a demand for a medicament whose active substance is highly available at the target organ (brain) and which is well tolerated, particularly in long-term therapy.

The use of frankincense is already known in folk medicine for treating the most different diseases, in particular inflammations and rheumatism, above all in Chinese and Indian folk medicine.

Frankincense or olibanum is understood to mean a gum resin which can be obtained from the bark of the trees *Boswellia carteri, Boswellia serrata* and other species domiciled in Arabia and Somalia. The resin usually contains 5 to 9% olibanum oil (or frankincense oil), 15 to 16% gum acids, 25 to 30% compounds insoluble in ether, and 45 to 55% compounds soluble in ether, in particular the triterpenoid boswellic acids, mostly the β-boswellic acid. Boswellic acid is also often referred to as *boswellia* acid in the literature.

A mixture of the resins of the balsam trees *Boswellia sacra* (South Arabia), *Boswellia carteri* and *Boswellia frereana* (both Somalia) is also often referred to as frankincense or olibanum. The Indian frankincense ("Salai Guggal") is also known. It is obtained from extracts of the *Boswellia serrata* resin (India). Salai Guggal is a vegetable mixture of many substances. It contains ethereal oils (various mono-, di-sesquiterpenes), mucilages (inter alia galactose, arabinose, mannose, xylose), and the resinous substances pharmacologically effective according to today's standard of knowledge (pentacyclic and tetracyclic triterpenes, boswellic acids or tirucallic acids). Following extraction with lipophilic solvents according to special methods (see below), what is called a "standardized Indian frankincense dry extract" is obtained.

Pardhy & Bhattacharyya report in Ind. J. Chem., 16 b: 176-178, 1978, that *Boswellia serrata* substantially contains the following ingredients: β-boswellic acid, acetyl-β-boswellic acid, acetyl-11-keto-β-boswellic acid, 11-keto-β-boswellic acid and small portions of α- and β-boswellic acid and the tirucallic acids.

In the recent past, several medical applications were found for frankincense or frankincense extract and in particular for boswellic acid and the derivatives thereof.

For example, WO 90/01937 reports that α-boswellic acid acetate and β-boswellic acid acetate and the analogs thereof inhibit topoisomerase I and topoisomerase II. Therefore, this publication proposes that the compounds be used for treating various types of cancer.

DE-A 42 01 903 and its equivalent EP-A 552 657 disclose that pure boswellic acid, physiologically acceptable salts thereof, derivatives thereof and salts of the derivatives or a boswellic acid-containing, vegetable preparation may combat inflammatory processes caused by an increased leukotriene formation. Therefore, said publications propose that the compounds be used in particular for treating inflammatory arthropathies, epidermal lesions, allergic and chronic asthma, endotoxin shock, inflammatory bowel diseases and chronic hepatitis.

DE-A 44 44 288 and its equivalent EP-B 0 796 103 disclose that frankincense, frankincense extracts, substances contained in frankincense, their physiologically acceptable salts, their derivatives and the physiological salts thereof, pure *boswellia* acid, a physiologically acceptable salt, a derivative and a salt of the derivative can be used for treating Alzheimer's disease.

DE-A 44 45 728 uses pure boswellic acid, physiologically acceptable salts thereof, derivatives thereof or salts of the derivatives and vegetable preparations containing a boswellic acid for the treatment of brain tumors.

WO 97/07796 uses *boswellia* acid, a physiologically acceptable salt, a derivative, a salt of the derivative or a boswellic acid-containing vegetable preparation for preventing and/or combating diseases which are caused by an increased leukocyte elastase or plasmin activity. Therefore, this publication proposes the use of compounds for treating diseases, such as pulmonary emphysema, acute respiratory distress syndrome, shock lung, cystic fibrosis, chronic bronchitis, glomerulonephritis and rheumatic arthritis, as well as for inhibiting the growth and metastasis formation of many types of tumor.

WO 02/15916 and DE-A 100 41 217 constituting its priority disclose dihydroboswellia acids, physiologically acceptable salts thereof and hydrogenated extracts from *boswellia*. Said publications suggest the use of these compounds for the prophylactic and/or therapeutic treatment of undesired physical and psychic conditions, in particular of somatic, psychosomatic and psychic diseases, such as inflammatory processes caused by increased leukotriene formation, leukocyte elastase or plasmin activity. The above-mentioned diseases are e.g. inflammatory arthropathies, epidermal lesions, allergic and chronic asthma, endotoxin shock, inflammatory bowel diseases, chronic hepatitis, pulmonary emphysema, acute respiratory distress syndrome, shock lung, cystic fibrosis, chronic bronchitis, glomerulonephritis and rheumatic arthritis as well as special tumors and tumor metastases.

None of said publications discloses that frankincense or hydrogenated frankincense products can be used for preventing and treating cerebral ischemia and/or cranial/brain trauma. Nor can it be derived from the literature that hydrogenated frankincense products are excellently suited for treating Alzheimer's disease.

It is thus an object of this invention to provide a medicament which can be used successfully for preventing and/or treating cerebral ischemia and/or cranial/brain trauma.

Another object of this invention is to provide a medicament which has a high bioavailability at the target organ and, along with an excellent effectiveness in the treatment of cerebral ischemia and cranial/brain trauma, can be used in a particularly advantageous way for treating Alzheimer's disease.

These objects are achieved by the subject matters of the claims.

The invention thus provides the use of frankincense, frankincense extracts, substances contained in frankincense, the physiologically acceptable salts thereof, their derivatives and the physiologically acceptable salts thereof, pure boswellic acid, a physiologically acceptable salt of boswellic acid, a derivative of boswellic acid, a salt of a boswellic acid derivative or a boswellic acid-containing vegetable preparation for the production of a medicament for the prophylactic and/or therapeutic treatment of cranial/brain trauma and/or cerebral ischemia, on the one hand, and the use of the hydrogenation products of frankincense extracts, substances contained in frankincense, the physiologically acceptable salts thereof, their derivatives and the physiologically acceptable salts thereof, pure boswellic acid, a physiologically acceptable salt of boswellic acid, a derivative of boswellic acid, a salt of a boswellic acid derivative or a boswellic acid-containing vegetable preparation for the production of a medicament for the prophylactic and/or therapeutic treatment of cerebral ischemia, cranial/brain trauma and/or Alzheimer's disease, on the other hand.

On account of their effectiveness in the prophylaxis and treatment of cerebral ischemia, the medicaments can also be used advantageously for preventing and treating cerebral lesions caused by apoplexy, cardiac infarction or after an operation.

It was found surprisingly that frankincense, in particular frankincense extracts, and substances contained in frankincense as well as the derivatives thereof, each in the salt form, where appropriate, and the hydrogenation products of the above compounds and active mixtures are excellently suited for preventing and/or treating cerebral ischemia and cranial/brain trauma.

Different from the literature, it is not only frankincense and frankincense extracts that can be used for treating Alzheimer's disease but also the above-mentioned hydrogenation products which in addition have a good bioavailability.

Although as pointed out above frankincense and frankincense products are known to be traditional natural drugs or medicaments for treating different psychic and physical conditions, the literature is silent on the availability, existing at the target organ (site of action), of the active substances contained therein. What is called the bioavailability is of special significance for the very prophylaxis and/or treatment of diseases pertaining to the brain. An active substance should be able to penetrate the blood-brain barrier, which may increase the effect and keep constant or reduce the dosage of the medicament. In addition, resorption in the intestine has to be adequate.

According to the invention, preferably acetyl-11-keto-β-boswellic acid (AKBA), 11-keto-β-boswellic acid (KBA) and β-boswellic acid are used as boswellic acid. β-boswellic acid may contain small amounts of α- or γ-boswellic acid. β-boswellic acid can be obtained in known manner from boswellic acid-containing plants, in particular from *Boswellia serrata*. Other suitable *boswellia* species are *Boswellia papyrifera, Boswellia frereana, Boswellia carteri, Boswellia thurifera* or *Boswellia glabra*. Yet, other representatives of the *boswellia* family may also be used.

Physiologically acceptable salts of boswellic acid are preferably sodium, potassium, ammonium and calcium salts. Preferred derivatives of boswellic acid are $C_1$-$C_6$ alkyl ester where the carboxyl group of boswellic acid was esterified with a corresponding alcohol. Methyl ester, ethyl ester, n-propylester, iso-propyl ester, n-butyl ester, iso-butyl ester and tert.-butyl ester are preferred. It is also possible for the hydroxyl group of boswellic acid to be esterified with a physiologically compatible carboxylic acid, preferably a $C_1$-$C_{20}$, in particular a $C_1$-$C_6$, carboxylic acid, in particular with formic acid or acetic acid. Boswellic acid derivatives preferably used according to the invention are β-boswellic acid acetate, β-boswellic acid formate, β-boswellic acid methyl ester, acetyl-β-boswellic acid, acetyl-11-keto-β-boswellic acid (AKBA) and 11-keto-β-boswellic acid (KBA).

According to the invention it is preferred to use vegetable preparations, in particular frankincense or frankincense extracts for the production of the medicaments for the prophylactic and/or therapeutic treatment of cerebral ischemia and/or cranial/brain trauma. The extracts preferably contain one or more of the above-mentioned compounds.

Thus, the use of frankincense or frankincense extracts, containing boswellic acid, in particular β-boswellic acid, for the production of a medicament for the prophylactic and/or therapeutic treatment of cerebral ischemia and/or cranial/brain trauma is preferred according to the invention.

Boswellic acids, in particular β-boswellic acid, can be obtained in known manner from plants containing boswellic acid, in particular from *Boswellia serrata*. Other suitable *boswellia* species are *Boswellia papyrifera, Boswellia frereana, Boswellia carteri, Boswellia thurifera* or *Boswellia glabra*. Yet, it is also possible to use other representatives of the *boswellia* family.

The frankincense used according to the invention or the frankincense extracts used according to the invention (e.g. Salai Guggal) preferably contain β-boswellic acid and/or acetyl-β-boswellic acid and/or acetyl-11-keto-β-boswellic acid and/or 11-keto-β-boswellic acid.

Vegetable preparations which can preferably be used according to the invention for the production of the medicaments for the prophylactic and/or therapeutic treatment of cerebral ischemia and/or cranial/brain trauma, are commercially available, e.g. from the company of Ayurmedica, Pöcking, Germany, e.g. under the designation of H15. This is a lipophilic extract from *Boswellia serrata* which contains an olibanum dry extract as the active substance. The product is available as a tablet or as granules. As shown in DE-A 44 44 288, a table contains 400 mg olibanum dry extract (4.2-5.9:1), extracting agent: chloroform/methanol. 1 g granules contain 500 mg olibanum dry extract (4.2-5.9:1), extracting agent: chloroform/methanol.

However, other preparations containing frankincense extract can also be used according to the invention. In particular it is possible to use according to the invention synthetically produced or naturally collected ingredients of frankincense, in particular acetyl-11-keto-β-boswellic acid and/or 11-keto-β-boswellic acid and/or α-boswellic acid, optionally in admixture with α- and/or γ-boswellic acid and/or one or more of the boswellic acid derivatives preferably used according to the invention, as described above, for the production of the medicament for the prophylactic and/or therapeutic treatment of cerebral ischemia and/or cranial/brain trauma according to the invention The active substances and active substance compositions which are preferred according to the invention and can be used for the production of the medicaments for the prophylactic and/or therapeutic treatment of cerebral ischemia and/or cranial/brain trauma, are described in DE-A 44 44 288 and DE-A 44 45 728, for example, to which reference is made in this respect. Boswellic acids and boswellic acid derivatives, preferred according to the invention, are also described in DE-A 42 01 903, to which reference is also made in this respect.

The active substances and active substance compositions which are described in DE-A 44 44 288 are preferred according to the invention.

A plant extract which was collected from frankincense, e.g. by ethanolic extraction, is also used preferably according to the invention According to the invention the medicament for the prophylactic and/or therapeutic treatment of cerebral ischemia and/or cranial/brain trauma may contain, in addition to the active substances defined herein and based on frankincense, further active substances, in particular further vegetable active substances.

According to the invention it was also found that the hydrogenation products of frankincense can be resorbed very well and penetrate adequately the blood-brain barrier so that an adequate active substance concentration can be achieved in the target organ, the activity of the products being substantially maintained, favorably even improved.

The hydrogenation products of frankincense, its ingredients and the physiologically acceptable salts and derivatives of these hydrogenation products and also hydrogenated frankincense extracts are suited for the production of an inventive medicament for the prophylactic and/or therapeutic treatment of cerebral ischemia, cranial/brain trauma and/or Alzheimer's disease.

Hydrogenation products of boswellic acid-containing vegetable extracts, boswellic acid, physiologically acceptable salts of boswellic acid, derivatives of boswellic acid, physiologically acceptable salts of these derivatives, boswellic acid-containing vegetable preparations or keto-boswellic acid-containing vegetable extracts are also suited according to the invention. Hydrogenation products of further ingredients of frankincense, such as tirucallic acid or other triterpenoid compounds, salts or derivatives thereof and vegetable extracts containing these compounds, are also suited.

The hydrogenation products of acetyl-11-keto-β-boswellic acid, 11-keto-β-boswellic acid or β-boswellic acid are also suited according to the invention, wherein the latter may contain small amounts of α- or γ-boswellic acid. Hydrogenation products of β-boswellic acid acetate, β-boswellic acid formate, β-boswellic acid methyl ester, acetyl-β-boswellic acid and boswellic acids and derivatives of boswellic acids which are described in DE-A 42 01 903, to which reference is made in this respect, are also suited according to the invention.

Dihydroboswellic acids, their physiologically acceptable salts, derivatives thereof and physiological salts of the derivatives, in particular β-dihydroboswellic acid acetate, β-dihydroboswellic acid formate, β-dihydroboswellic acid methyl ester, acetyl-β-dihydroboswellic acid, α-dihydroboswellic acid, acetyl-α-dihydroboswellic acid and formyl-α-dihydroboswellic acid can be used as hydrogenation products according to the invention.

Keto-dihydroboswellic acids, their physiologically acceptable salts, derivatives thereof and physiological salts of the derivatives, in particular acetyl-11-keto-β-dihydroboswellic acid, 11-keto-β-dihydroboswellic acid or formyl-11-keto-β-dihydroboswellic acid are also suited according to the invention.

The hydrogenation products usable according to the invention can be obtained by hydrogenation, preferably by catalytic hydrogenation. These compounds are hydrogenated in a manner known to a person skilled in the art, preferably such that the skeletal structure of the compound is hydrogenated selectively. Such a method is described in WO 02/15916, for example.

A hydrogenated plant extract which is obtained from frankincense, e.g. by ethanolic extraction, can be used for the production of an inventive medicament for the prophylactic and/or therapeutic treatment of cerebral ischemia and/or cranial/brain trauma and/or Alzheimer's disease.

The sodium, potassium, ammonium and calcium salts of the above-mentioned compounds are to be physiologically acceptable salts of the hydrogenation products according to the invention. The derivatives are to be in particular the $C_1$-$C_6$ alkyl esters of dihydroboswellic acid where the carboxyl group of dihydroboswellic acid was esterified with a corresponding alcohol. Such dihydroboswellic acid alkyl esters are e.g. the methyl ester, ethyl ester, n-propyl ester, iso-propyl ester, n-butyl ester, iso-butyl ester and tert.-butyl ester. It is also possible for the hydroxyl group of dihydroboswellic acid to be esterified with a physiologically compatible carboxylic acid, e.g. with a $C_1$ to $C_{20}$ carboxylic acid, in particular with a $C_1$-$C_6$ carboxylic acid, in particular with formic acid or acetic acid.

Vegetable preparations which can be used for the production of the hydrogenation products according to the invention, are commercially available, in particular from the company of Ayurmedica, Pöcking, Germany, e.g. under the designation of H15.

However, hydrogenation products of other preparations with frankincense extract can also be used according to the invention. In particular it is possible to use according to the invention hydrogenation products of synthetically produced or naturally collected ingredients of frankincense, in particular acetyl-11-keto-β-boswellic acid and/or 11-keto-β-boswellic acid and/or β-boswellic acid, optionally in admixture with α- and/or γ-boswellic acid and/or one or more of the boswellic acid derivatives preferably used according to the invention, as described above, for the production of the medicament.

Active substances and active substance compositions which are suited according to the invention and can be used for the production of the inventive medicaments containing the hydrogenation products, are described in WO 02/15916, for example, to which reference is made in this respect.

In addition to the active substances defined herein and based on frankincense, the medicament for the prophylactic and/or therapeutic treatment of cerebral ischemia and/or cranial/brain trauma and/or Alzheimer's disease can contain further active substances, in particular further vegetable active substances, according to the invention.

However, hydrogenation products of other preparations containing frankincense extract can also be used according to the invention. In particular it is possible to use according to the invention hydrogenation products of synthetically produced or naturally obtained ingredients of frankincense, in particular acetyl-11-keto-β-boswellic acid and/or 11-keto-β-boswellic acid and/or β-boswellic acid, optionally in admixture with α- and/or γ-boswellic acid and/or one or more of the boswellic acid derivatives preferably used according to the invention, as described above, for the production of the medicament.

Since the above frankincense products and the hydrogenated frankincense products have a very low toxicity, their compatibility is usually good. Subject to the severity of the disease to be treated and further factors, such as the duration of the disease, possible known patient's incompatibilities, the patient's general condition, etc., the dosages can easily be chosen by the attending physician. According to the invention the medicament is preferably formulated such that it is available in unit doses which can be administered, preferably orally, once or several times daily, in particular one to four times per day.

According to the invention the medicaments can be formulated in known manner for common administration routes, e.g. as oral, parenteral, rectal, intranasal, intracranial or intrathecal administrations. Oral, parenteral, rectal and intranasal administrations are preferred herein. The formulations can also be made for inhalation or insufflation. Formulations for the intracranial or intrathecal administration are also possible The medicaments according to the invention can be present in solid, semi-solid or liquid form, for example. They may be formulated as tablets, granules or capsules, for example, which along with the active substance or the active substance extract also contain pharmaceutically compatible additives, such as binders, fillers, lubricants, blasting or optionally wetting agents and which may be coated.

Medicaments present in the form of tablets or granules or pellets are preferred according to the invention, the granules or pellets usually being present in conventional capsules. Along with the active substance or the active substance extract the granules or tablets contain conventional pharmaceutically acceptable additives, such as binders, e.g. pregelatinized corn starch, polyvinyl pyrrolidone or hydroxypropylmethyl cellulose, fillers, such as lactose, saccharose, mannitol, corn starch, microcrystalline cellulose or calcium hydrogen phosphate, lubricants, such as stearic acid, polyethylene glycol, magnesium stearate, talcum or silicon dioxide, blasting agents, such as potato starch, sodium starch glycolate or sodium carboxymethyl cellulose and in particular the known superdisintegrating agents and optionally wetting agents, such as sodium lauryl sulfate. Tablets, pellets or capsules may be coated in known manner (e.g. with a water-soluble or an enteric coating) or they can be available without coating. Coated tablets are preferred.

Furthermore, the medicaments may be available in a manner known to the person skilled in the art as liquid preparations for the oral administration. Liquid preparations for oral administration may be present as aqueous or oily solutions, syrups, elixiers, emulsions or suspensions, for example. Formulations can also be available as dry product for reconstitution with a suitable solvent, in particular water. The production of such liquid preparations is also known and, where appropriate, conventional additives may be present, which include suspending agents, such as sorbitol, cellulose derivatives, glucose, sugar syrup, gelatin, aluminum stearate gel or hydrogenated cooking fats, emulsifiers, such as lecithin, gum Arabic or sorbitan monooleate, non-aqueous carriers, such as almond oil, oily esters, ethyl alcohol or fractionated vegetable oils, preservatives, such as methyl or propyl-para-hydroxybenzoate or sorbic acid, buffers, gustatory substances and flavoring agents, coloring substances and sweetening agents.

Medicaments according to the invention can also be formulated in known manner as preparations for injections. Preparations preferred according to the invention are preparations for injections, in particular for the intravenous, intramuscular, subcutaneous, intrathecal or intracranial injection, which are suitably available in unit dose form, such as ampoules, or in multiple-dose containers. The formulations optionally contain a conventional preservative and further conventional auxiliary substances. The medicaments according to the invention can also be prepared as suspensions, solutions or emulsions in oily or aqueous carriers in a manner known to the person skilled in the art. For example, the preparations may be available as suspensions, solutions or emulsions in oily or aqueous carriers and contain conventional auxiliary substances, such as suspending, stabilizing and/or dispersing agents and/or agents for adjusting the tonicity. Here, the agent can also be present as a dry powder for reconstitution in a suitable carrier.

Liquid sprays, nose drops or snuff powder can be mentioned as intranasal medicaments.

If the administration is to be effected by inhalation, the compounds are provided e.g. as an aerosol spray. For example, the compounds or extracts according to the invention may be available using suitable propellants in pressurized packs. In this case, the pack will also contain a suitable dosing apparatus. Capsules or cartridges made of gelatin, for example, for use in an inhalation means or an insufflation means may be prepared conventionally by using a powder mixture of a compound used according to the invention and a suitable powdery parent substance, such as lactose or starch.

Examples of suitable formulations and processes for the production thereof are found in DE-A 44 44 288 and DE-A 44 45 728, to the full contents of which reference is made in this respect. In particular, reference is made to the examples of DE-A 44 44 288. The medicaments can be formulated correspondingly according to the invention.

The neuroprotective effect of frankincense extract containing boswellic acid on the infarct volume after experimentally induced transient focal cerebral ischemia (apoplexy) was checked as follows.

Experimental Induction of a Focal Ischemia by Intracerebral Microinjection of Endothelin 1 in the Vicinity of the Middle Cerebral Artery (eMCAO)

Sprague Dawley rats (250-280 g) are clamped into a stereotactic device of the head under halothane inhalation narcosis and the skin is opened in the cranial center. A hole (1 mm in diameter) is drilled into the cranial bone using a dental drill in accordance with the coordinates: 0.90 mm anterior bregma, 5.2 mm lateral relative to satura sagittalis. A Hamilton syringe is then immersed to a depth of 7.5 mm into the brain from the dura mater and 3 µl (90 pmol) endothelin 1 is injected into the vicinity of the middle cerebral artery. Endothelin 1 has a vasoconstrictive effect so that the vessel is closed and apoplexy is induced. After 5 minutes, the syringe is removed and the skin above the cranial bone is sutured. The animals are held normothermically during the entire operation.

Experimental Groups:

Group 1: (n=8) eMCAO and frankincense extract (10 mg/kg, intraperitoneal, i.p., injection) 2 h before ischemia is induced, 6 h (10 mg/kg, i.p.) after the reperfusion, on day 3 (10 mg/kg, i.p.) and on day 6 (10 mg/kg, i.p.).

Group 2: (n=8) eMCAO and solvent (0.9% NaCl with 10% ethanol) i.p. injection as described in group 1.

Group 3: (n=8) mock-operated control group.

Group 4: (n=8) mechanical lesion induced by the injection channel of the Hamilton syringe.

Determining the Infarct Volume:

Having survived for 7 days, the animals are perfusion-fixed in deep pentobarbital narcosis using 4% paraformaldehyde in 0.1 M phosphate buffer. The brains are removed and coronal sections having a thickness of 1 mm are made in a rat brain matrix. Following cryoprotection in 30% sucrose, cryostat sections having a thickness of 20 µm are made, placed on slides and stained using toluidine Nissl. The cortical and striatal infarct centers are determined by means of a light microscope (Nikon, Eclipse TE 3000) with the image analysis software Lucia version 4.2.1, and the infarct volume is calculated by multiplication with the section thickness. The data is analyzed by means of the student's t-test for statistical significance.

Results:

When the middle cerebral artery is obstructed, nerve cells in the brain centers of cortex and striatum die off. 7 days after the induction of cerebral ischemia and parallel administration of frankincense extract, a marked and significant reduction of the infarct volume can be observed in comparison with the untreated control group. This finding is surprising and novel.

Hence it has been proved that the medicaments produced according to the invention can reduce the lesion of cerebral tissue and resulting neurological peculiarities on account of an ischemia or can prevent such a lesion.

The neuroprotective effect of frankincense extract containing boswellic acid on brain injuries was checked as follows.

Experimental Induction of a Traumatic Brain Injury

First, a traumatic brain injury was induced experimentally to experimental animals in accordance with what is called the fluid percussion method. To this end, Sprague Dawley rats (250 to 280 g) were clamped into a stereotactic device of the head under halothane inhalation narcosis, and the skin was opened in the cranial center. A hole of 5 mm (diameter) is drilled into the cranial bone of the right calotte between bregma and lambda by means of a dental drill, the dura mater remaining intact. Via a plexiglass cylinder filled with isotonic saline and connected with the trepanation hole, a defined metal weight deflects the pin of the plexiglass cylinder. As a result, the intracranial pressure is rapidly increased so as to cause an injury of cortical and striatal brain centers. Having induced the traumatic brain injury, the skin above the cranial bone is sutured. The animals were held normothermically during the entire operation.

Experimental Groups:

Four experimental groups comprising eight experimental animals each were created. Two hours before ischemia was induced, six hours after the reperfusion, on the third day after the operation and on the sixth day after the operation, group 1 was given intraperitoneally 10 mg/kg frankincense extract each. Instead of the frankincense extract, group 2 was given intraperitoneally an aqueous solution containing 10% ethanol and 0.9% sodium chloride, an administration scheme being used the same as that of group 1. Group 3 was not treated—neither with frankincense extract nor with solvent—and group 4 was a control group where no ischemia was induced.

Determining the Trauma Volume:

Having survived for seven days, the animals were perfusion-fixed in deep pentobarbital narcosis using 4% paraformaldehyde in 0.1 M phosphate buffer, and the infarct volume was determined. For this purpose, the brains were removed and coronal sections having a thickness of 1 mm were made in a rat brain matrix. Following cryoprotection in 30% sucrose, cryostat sections having a thickness of 20 µm were made, placed on a slide and stained using toluidine Nissl. The cortical and striatal infarct centers were determined by means of a light microscope (Nikon, Eclipse TE 3000) with the image analysis software Lucia version 4.2.1, and the trauma volume was calculated by multiplication with the section thickness. The data was analyzed by means of the student's t-test for statistical significance.

Results:

As a result of the experimentally induced brain trauma, nerve cells in the brain centers of cortex and striatum died off. Seven days after the induction of the cerebral ischemia and administration of frankincense extract, a marked and significant reduction of the trauma-induced lesions can be observed in comparison with the untreated control group.

Hence it has been proved that the medicaments produced according to the invention can reduce the lesion of cerebral tissue and resulting neurological peculiarities on account of a cranial/brain trauma or can prevent such a lesion.

The invention claimed is:

1. A method of reducing a lesion of cerebral tissue induced by cerebral ischemia, wherein the cerebral ischemia occurs as a result of aploplexy, said method comprising the step of administering to a subject in need thereof a medicament comprising a neuroprotective amount of a hydrogenation product obtained through the catalytic hydrogenation of an ethanol extract of frankincense (*Boswellia serrata*).

2. The method according to claim 1, wherein the frankincense extract comprises one or more compounds selected from the group consisting of a keto-boswellic acid, 3-O-acetyl-11-keto-β-boswellic acid, 11-keto-β-boswellic acid, a physiologically acceptable salt of a keto-boswellic acid, a derivative of a keto-boswellic acid, and a salt of a keto-boswellic acid derivative.

3. The method according to claim 1, wherein the frankincense extract comprises a tirucallic acid, another triterpene or a salt or derivative thereof.

4. The method according to claim 1, wherein the frankincense extract comprises an extract from *Boswellia serrata* resin.

5. A method of reducing a lesion of cerebral tissue induced by a cranial/brain trauma or, a short-term cerebral ischemia resulting from apoplexy or cardiac infarction, said method comprising the step of administering to a subject in need thereof a medicament comprising a neuroprotective amount of a hydrogenation product of a frankincense extract or a physiologically acceptable salt of said hydrogenation product.

6. The method according to claim 5, wherein the frankincense extract comprises an extract from *Boswellia serrata* resin.

7. The method according to claim 1, wherein the medicament is formulated for intraperitoneal, oral, buccal, rectal, intramuscular, topical, subcutaneous, intraarticular, intravenous, intrathecal or intracranial administration.

8. The method according to claim 1, wherein the medicament comprises a tablet or solution.

9. The method according to claim 5, wherein the medicament is formulated for intraperitoneal, oral, buccal, rectal, intramuscular, topical, subcutaneous, intraarticular, intravenous, intrathecal or intracranial administration.

10. The method according to claim 5, wherein the medicament comprises a tablet or solution.

\* \* \* \* \*